(12) United States Patent
Coopersmith

(10) Patent No.: US 7,806,125 B2
(45) Date of Patent: Oct. 5, 2010

(54) INTER DENTAL TOOTH CLEANER AND DELIVERY DEVICE

(75) Inventor: Allan Coopersmith, 5757 Ave. Decelles, Suite 520, Montreal, Quebec (CA) H3S 2C3

(73) Assignee: Allan Coopersmith, Montreal (CA)

( * ) Notice: Subject to any disclaimer, the term of this patent is extended or adjusted under 35 U.S.C. 154(b) by 0 days.

(21) Appl. No.: 11/205,251

(22) Filed: Aug. 17, 2005

(65) Prior Publication Data

US 2006/0174910 A1   Aug. 10, 2006

Related U.S. Application Data

(60) Provisional application No. 60/602,007, filed on Aug. 17, 2004.

(51) Int. Cl.
*A61C 15/00* (2006.01)

(52) U.S. Cl. ........................... 132/329; 132/322

(58) Field of Classification Search ............. 433/216, 433/141, 142, 25, 80, 81, 102, 143, 164, 433/165, 166; 132/308, 321, 329, 322, 323–228; 15/167.1; 118/200; 604/77; 401/27, 122, 401/126, 129, 130
See application file for complete search history.

(56) References Cited

U.S. PATENT DOCUMENTS

| | | | |
|---|---|---|---|
| 1,969,808 A * | 8/1934 | Lentulo | 433/164 |
| 4,032,803 A | 6/1977 | Durr et al. | |
| 4,219,619 A | 8/1980 | Zarow | |
| 4,274,771 A * | 6/1981 | Nishimura | 408/230 |
| 4,462,136 A | 7/1984 | Nakao | |
| 4,514,174 A | 4/1985 | Dougherty | |
| 4,608,021 A | 8/1986 | Barrett | |
| 4,679,274 A | 7/1987 | Friedman | |
| 4,712,266 A * | 12/1987 | Yamaki | 15/167.1 |
| 4,828,420 A * | 5/1989 | Otsuka et al. | 401/268 |
| 4,850,875 A | 7/1989 | Takatsu | |
| 4,911,187 A | 3/1990 | Castillo | |
| 5,123,841 A | 6/1992 | Millner | |
| 5,125,834 A | 6/1992 | Swan | |
| 5,133,661 A | 7/1992 | Euvrard | |
| 5,219,284 A * | 6/1993 | Velvart et al. | 433/102 |
| 5,283,924 A | 2/1994 | Kaminski | |
| 5,377,377 A * | 1/1995 | Bredall et al. | 15/167.1 |
| 5,609,170 A | 3/1997 | Roth | |
| 5,639,238 A | 6/1997 | Fishburne, Jr. | |
| 5,647,851 A | 7/1997 | Pokras | |
| 5,704,388 A | 1/1998 | Freeman | |
| 5,735,689 A * | 4/1998 | McSpadden | 433/102 |
| 5,755,572 A | 5/1998 | Bab | |
| 5,775,346 A | 7/1998 | Szyszkowski | |

(Continued)

*Primary Examiner*—Cris L Rodriguez
*Assistant Examiner*—Michael R Ballinger
(74) *Attorney, Agent, or Firm*—Olser, Hoskin & Harcourt LLP

(57) ABSTRACT

An inter dental device which is a tooth cleaner and gum massager which cleans the area between anterior and posterior teeth, comprising a handle and a stem and flanges and a tip which is grooved or twisted in a spiral pattern, and the flanges extending from a central stem are arranged in a spiral pattern which is continuous with the spiral pattern of the grooves of the tip. This device also may serve as a delivery device which holds and delivers substances to the area between teeth, and does not remove said substances as the device is withdrawn.

21 Claims, 12 Drawing Sheets

U.S. PATENT DOCUMENTS

| | | |
|---|---|---|
| 5,839,895 A | 11/1998 | Fishburne, Jr. |
| 5,842,862 A * | 12/1998 | Nissan ........................ 433/102 |
| 5,851,116 A | 12/1998 | Margolis |
| 358,684 A | 7/1999 | Summer |
| 6,142,778 A | 11/2000 | Summer |
| 6,171,108 B1 * | 1/2001 | Roane ........................ 433/224 |
| 6,257,889 B1 * | 7/2001 | Boston ........................ 433/165 |
| 6,418,940 B1 * | 7/2002 | Tcherny et al. ............. 132/321 |
| 6,545,390 B1 | 4/2003 | Hahn et al. |
| 6,579,082 B2 * | 6/2003 | Castellari ................... 425/150 |
| 6,602,229 B2 | 8/2003 | Coss |
| 6,638,067 B2 * | 10/2003 | Fischer et al. ............... 433/102 |
| 6,648,561 B2 * | 11/2003 | Kraemer ...................... 408/57 |
| 6,702,579 B1 * | 3/2004 | Hoppe et al. ................. 433/102 |
| 6,860,737 B2 | 3/2005 | Uls. |
| 6,932,604 B2 | 8/2005 | Han |
| 7,018,205 B2 * | 3/2006 | Abel ........................... 433/102 |
| 7,025,986 B2 | 4/2006 | Brown |
| 7,033,101 B2 | 4/2006 | Han |
| 2003/0176531 A1 | 9/2003 | Kassab |
| 2003/0224320 A1 | 12/2003 | Kandelman |
| 2004/0214135 A1 * | 10/2004 | Ruddle ....................... 433/102 |

* cited by examiner

INTER DENTAL TOOTH CLEANER AND DELIVERY DEVICE

CROSS-REFERENCE TO RELATED APPLICATIONS

The present application claims the benefit of U.S. provisional Patent Application Ser. No. 60/602,007 filed on Aug. 17, 2004 entitled Interprox™. The contents of which are incorporated herein by reference.

FIELD OF INVENTION

The present invention relates to an a inter dental device which is a tooth cleaner which cleans the area between anterior and posterior teeth, comprising a handle and stem and flanges and tip, and the flanges extending from a central stem, said flanges arranged in a spiral pattern and tip grooved or twisted to form a spiral pattern continuous with the flange spiral. The twisted spiral grooves and flanges serve to remove bacteria, food and debris when said device is rotated clockwise and also serve to hold substances such as, but not limited to, medicaments and antiseptics within the spirals and grooves, and said substances which can be deposited between teeth when the device is rotated counterclockwise without removing said substances as the device is withdrawn. The handle as well as the cover of said device can be used as a reservoir for said substances. The device can be inserted into a motorized handle so that it can be rotated clockwise or counterclockwise.

BACKGROUND OF THE INVENTION

The area between the teeth which is referred to as the inter dental area is the area which is most prone to plaque accumulation and periodontal breakdown and dental caries because it is the area of the mouth which is the most difficult to clean.

The inter dental area refers to the inter proximal area which is the area between adjacent teeth which consists of the roots of the teeth which are covered in cementum which overlies the dentin surface. Often the cementum is erroded or abraded leaving the underlying soft vulnerable dentin surface exposed leading to hypersensitivity or caries. This is the area also most vulnerable to plaque accumulation leading to periodontal breakdown.

Most devices designed to clean this inter dental area require manual dexterity, are difficult to use, take too much time, are painful, inefficient, tear or break easily, are expensive and therefore contribute to poor compliance by the patient. Dental floss is difficult to use and does not adequately clean the inter dental areas especially when some periodontal breakdown has already occurred. Currently most inter dental devices are brushes which are commonly made from nylon bristles which have been inserted into a twisted wire stem. These brushes are fragile and break frequently. The wire can scratch and irritate the fragile root surface as well as dental restorations and implants. They are often too wide to fit comfortably between the teeth. Other inter dental cleaners which are shaped like wedges can clean only by a push/pull technique and often leave plaque and debris behind.

Kandleman designed an inter dental cleaner to clean the inter proximal area and then deposit medicaments or antiseptics to said areas without removing said medicaments or antiseptics as the device is withdrawn. His device is inefficient and the applicator section is too long and is redundant and useless when the device is used only to clean the inter proximal areas and will jab and interfere with the tongue and cheeks as it cleans between the teeth. Furthermore the applicator must be thick enough to contain holes connecting to a hollow channel to deliver said medicaments so that it will bend and not adequately fit the small area between anterior and crowded teeth. At the same time the applicator must be thin yet rigid enough to guide the device through the narrow inter dental space. The Kandleman device would require an excessively large handle to hold enough material to treat the entire mouth and cannot be refilled easily (with an eye dropper effect) through the tip which is too narrow with holes that are too small and the distance from the tip to the semi rigid deformable handle is too long. The Kandleman device needs an additional section which is an applicator which is different from the cleaning section. This applicator section is redundant, especially if it is used for cleaning between the teeth, and is complicated and expensive to manufacture.

SUMMARY OF THE INVENTION

There is therefore a need for a dental device which is an inter dental cleaner which can fit into both large, medium and small inter dental areas, and may also deliver materials for instance, but not limited to, medicaments or antiseptics to the area between teeth without removing said materials as the device is withdrawn from the inter proximal area. In all cases as mentioned in this patent, the inter dental area or the area between teeth or the inter proximal area may refer to the teeth surfaces between teeth including but not limited to dentin, enamel, cementum, the gingiva, the sub gingival sulcus, and the periodontal pocket. This device should be simple and inexpensive and easy to manufacture and to use and should fit between large and small inter dental spaces. The material should be stored or carried and then released easily by said device. It is preferred that the applicator section need not be different from the cleaning section. The device should be easily refillable so that the entire mouth may be treated. This device should be easily attachable to a motorized device which could facilitate its use and functionality. It could be used by the dentist in office or given to the patient for use at home.

The invention specifically lies in that the device is designed to clean between the teeth using flanges and grooves which are arranged in an uninterrupted continuous spiral so that it can be easily inserted between teeth and when the handle is rotated clockwise, the grooves and the spiral engage and clean the inter proximal surfaces of adjacent teeth and as the device is further rotated, food debris, plaque etc., is directed away from the inter dental space by the continuous spiral arrangement of grooves and flanges, allowing for an efficient.

It is a preferred embodiment of this invention that two helices which are slightly offset from one another are arranged in a spiral manner to more efficiently clean and distribute substances to the inter proximal area.

The uninterrupted continuation of the spiral in the groove of the tip extending to the spiral in the flange allows for a continuous flow of plaque, food, debris etc., out of the inter dental space when the device is rotated clock wise, and the continuous flow of medicaments into the inter proximal space when the device is rotated counter clockwise.

The spiral structure of the grooved tip allows for cleaning and removal of plaque, food and debris as the device is rotated or pulled and pushed, or twisted then pulled, and because the central shaft of the tip is solid, it can be made small and narrow enough to fit into the narrowest inter dental spaces found frequently with anterior teeth and crowded situations. There is no exposed wire or metal which can injure the periodontal tissue or cementum, dentin, and would therefore be safe for use with implants.

Another mode of action is when the handle is rotated clockwise, the grooves and the spiral engage the inter proximal surfaces of adjacent teeth and as the device is further rotated, the device is drawn deeper between the teeth (in a screw like manner), and as resistance is felt, the device is then pulled out from between the teeth bringing with it food, debris and plaque etc. in a "twist and pull" motion.

Conversely, when the handle of the device is rotated counter clockwise, the spiral pattern of the flanges which are continuous with the grooves in the tip, the mode of action is such that any material which is held or stored in the grooves or flanges is carried or deposited thoroughly into the area between the teeth and remains there without being withdrawn as the device is removed from between the teeth while being rotated counter clockwise.

The grooves in the channels and the spaces between the flanges serve to increase the surface area and facilitate both the cleaning and removal of plaque, food and debris, etc., as well as the retention of material (medicaments, antiseptics, etc., which can be delivered to the inter dental area. The uninterrupted continuous nature of the spiral of the grooves and the spiral of the flanges also facilitates these actions. The material can be loaded into the grooves and spaces between the flanges by dipping the device into said material and returning it to the mouth to be placed into the inter dental area without dripping or spilling. The cap or cover of the inter dental device can be loaded with material and as the device is withdrawn from said cap or container the material is loaded in the grooves and flanges ready for delivery to the inter dental area. The cap can also have a reservoir to hold additional material associated with it.

The handle and stem can be hollow and continuous thereby allowing for the storage of material in the handle. As the handle is squeezed the material travels down the hollow stem out the holes between the flanges and as the handle is rotated counterclockwise, the material travels from the middle of the device (thick and strong enough to accommodate a hollow stem and holes) towards the tip which is solid and thin enough so that it can be inserted between anterior and crowded teeth with small inter dental spaces.

The device can be easily inserted into a motorized device which allows for clockwise and counterclockwise rotation. The motorized device produces cleaning and massaging of the gums while utilizing a "screw like" action routing and removing plaque and debris and food etc. from between the teeth.

As embodied and broadly described herein the present invention provides a device which is an inter dental cleaner which cleans and massages the area between teeth and a delivery device which holds and delivers substances for instance, but not limited to, medicaments or antiseptics, to the area between teeth, and does not remove said substances as the device is withdrawn.

Other objects and features will become apparent by reference to the following description and the drawings.

For small inter proximal areas such as found between anterior or crowded teeth in which only the narrow tip of the device will fit, the substance travels out the holes between the flanges and is carried or transported to the tip of the device by the channels within the grooves which is continuous with the spiral flanges, and said material is carried or transported to the inter proximal area and is deposited there. As the handle continues to be turned counterclockwise, said material is left between the teeth and is not withdrawn as the device is removed.

Figure 7:
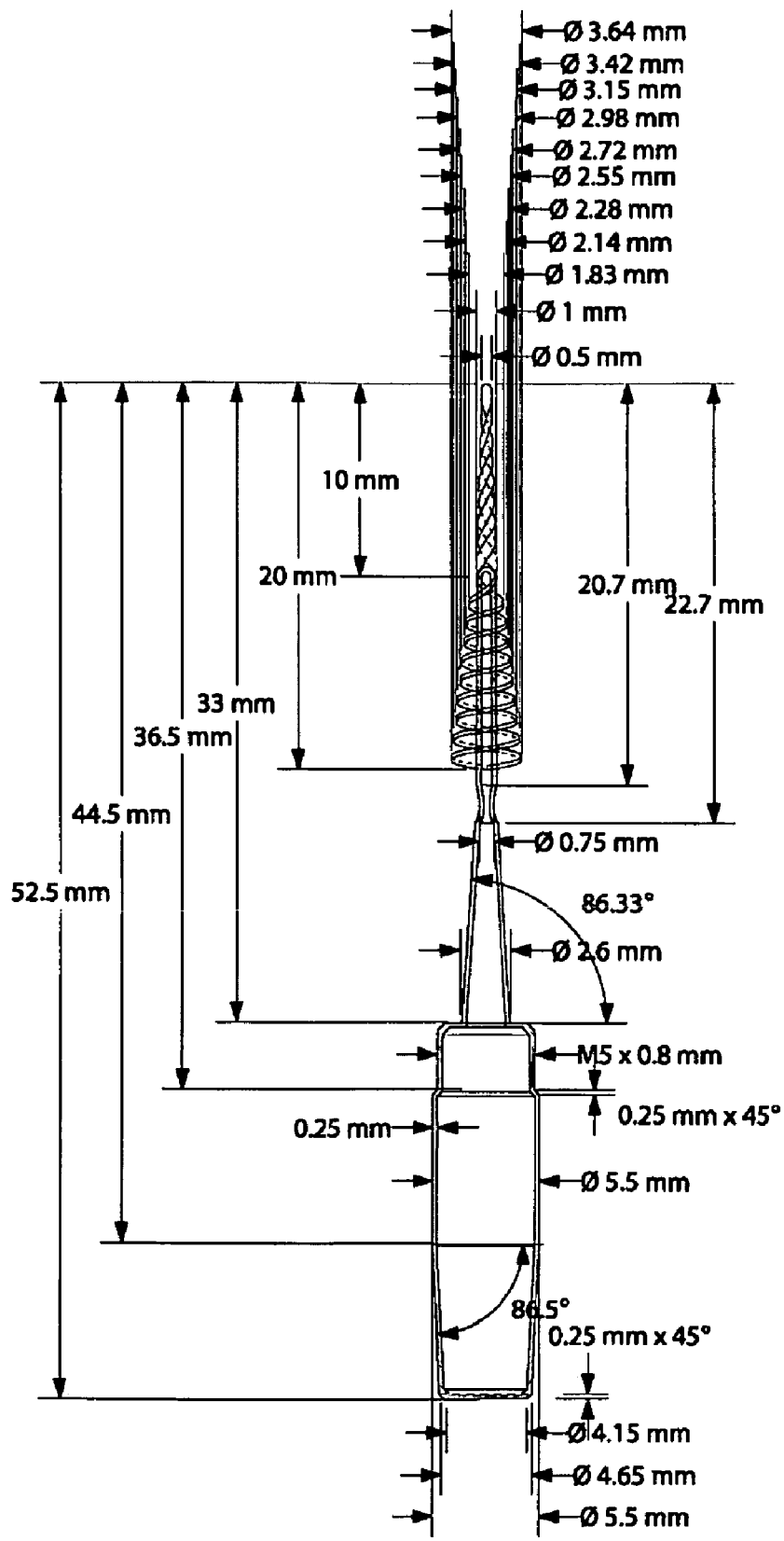

FIG. 7. Refers to the longitudinal cross section a preferred embodiment of the tooth cleaner/drug delivery dispenser.

Figure 8:
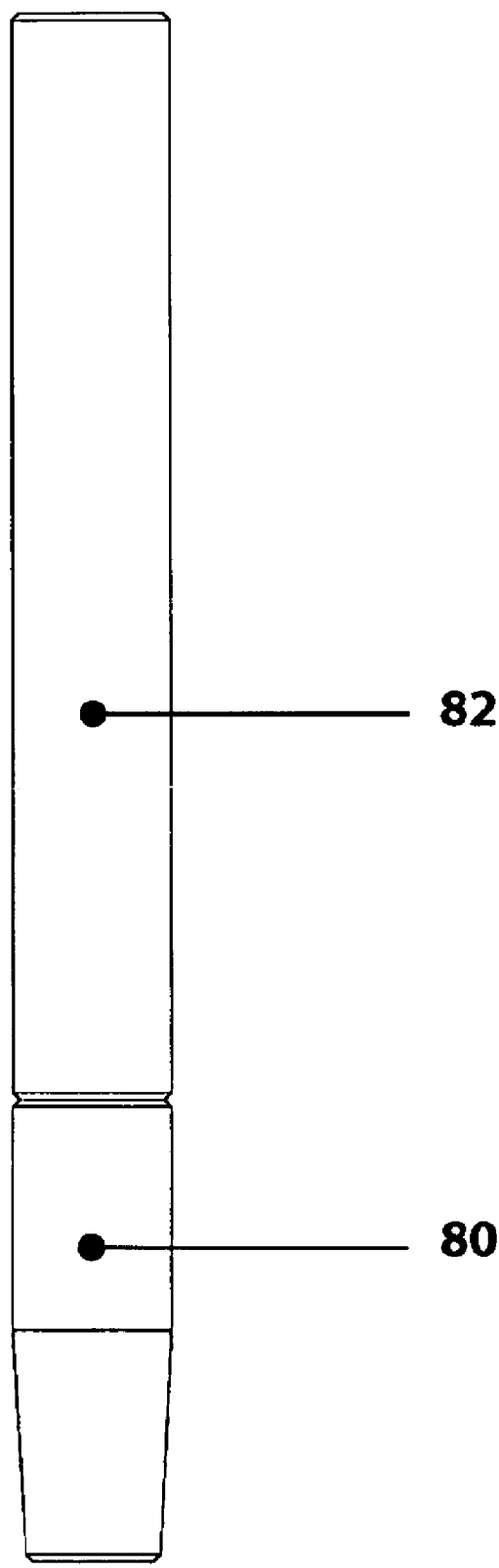

FIG. 8. Refers to the side view of the tooth cleaner/drug delivery dispenser which is covered by a cover which may contain a substance for instance but not limited to a medicament or antiseptic or fluoride or varnish, as indicated in FIG. 6.

Figure 9:
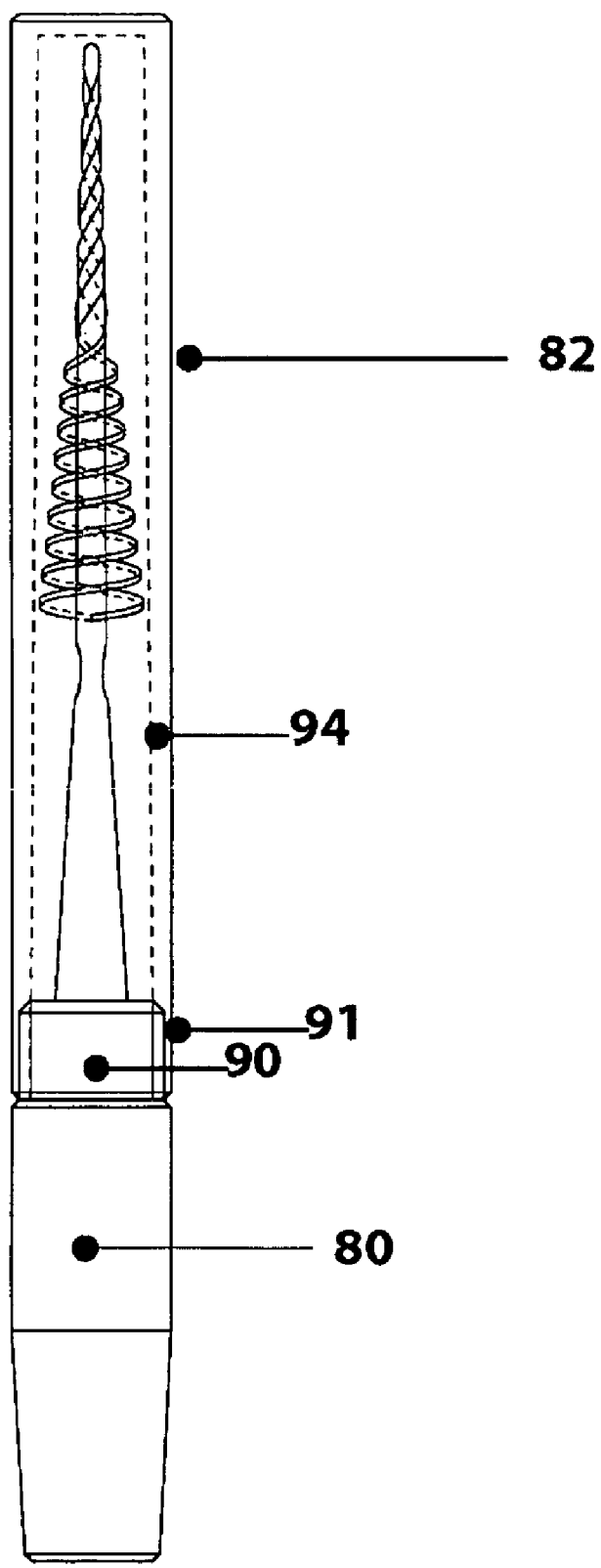

FIG. 9 refers to FIG. 8 with the cover being cut in a longitudinal cross section so that the tooth cleaner/drug delivery dispenser can be seen inside the cover. This cover may contain a substance as in FIG. 6 and when dipped into this container and then withdrawn, the substance is retained in the flanges and grooves of the stem and tip respectively and can now be transported and deposited into the area between the teeth as said device holding the substance is inserted into the inter dental space and rotated counterclockwise.

Figure 10:
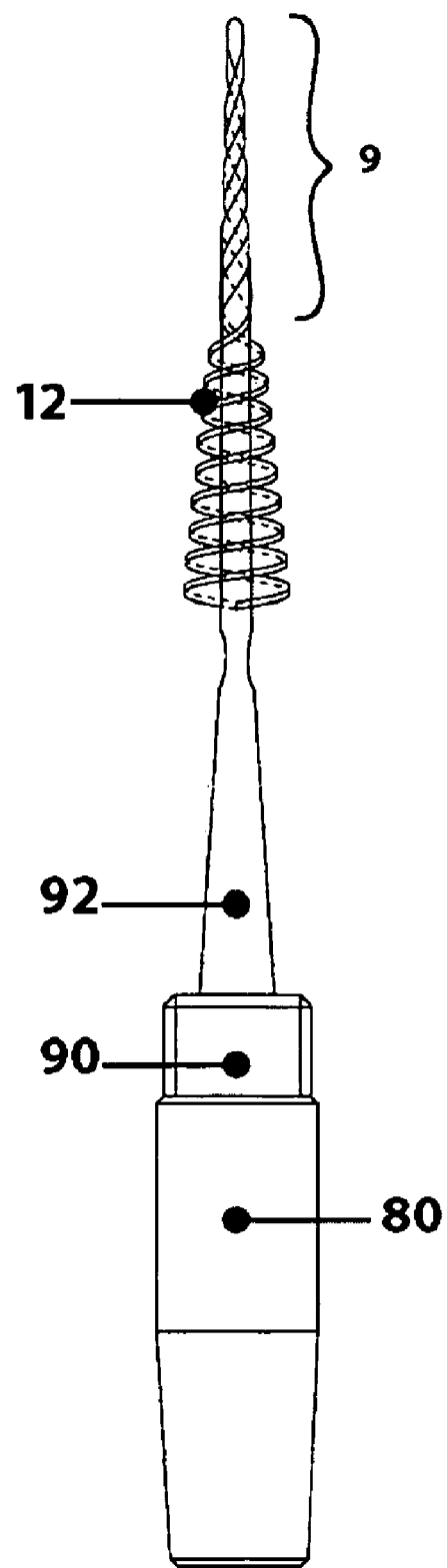

FIG. 10 refers to a side view of the tooth cleaner/drug delivery dispenser.

Figure 6:
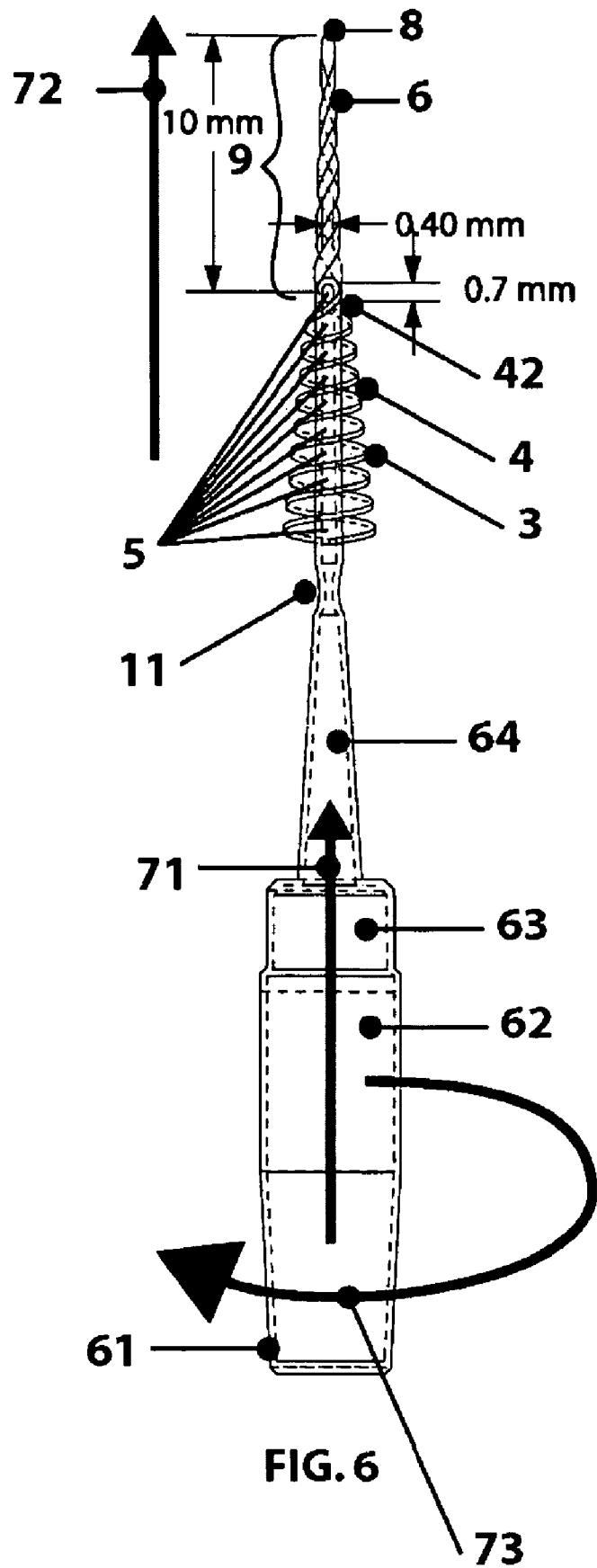
FIG. 6 demonstrates a side view of the Tooth cleaner/drug delivery device indicating a handle and stem that are rigidly deformable and contain a continuous hollow chamber extending from said handle through the stem and connect to holes in the stem between the flanges so that when the handle, which contains a substance for instance but not limited to a medicament or antiseptic or fluoride or varnish, is squeezed, positive pressure is exerted on said substance which travels down the stem and out the holes between the flanges. As the handle is rotated counterclockwise, said substance is pushed or transported along the channels formed by the spiral arrangement of said flanges towards the tip of the device and then is deposited in the area between the teeth and as the handle continues to be turned counterclockwise, said material is left between the teeth and is not withdrawn as the device is removed.
Figure 11:
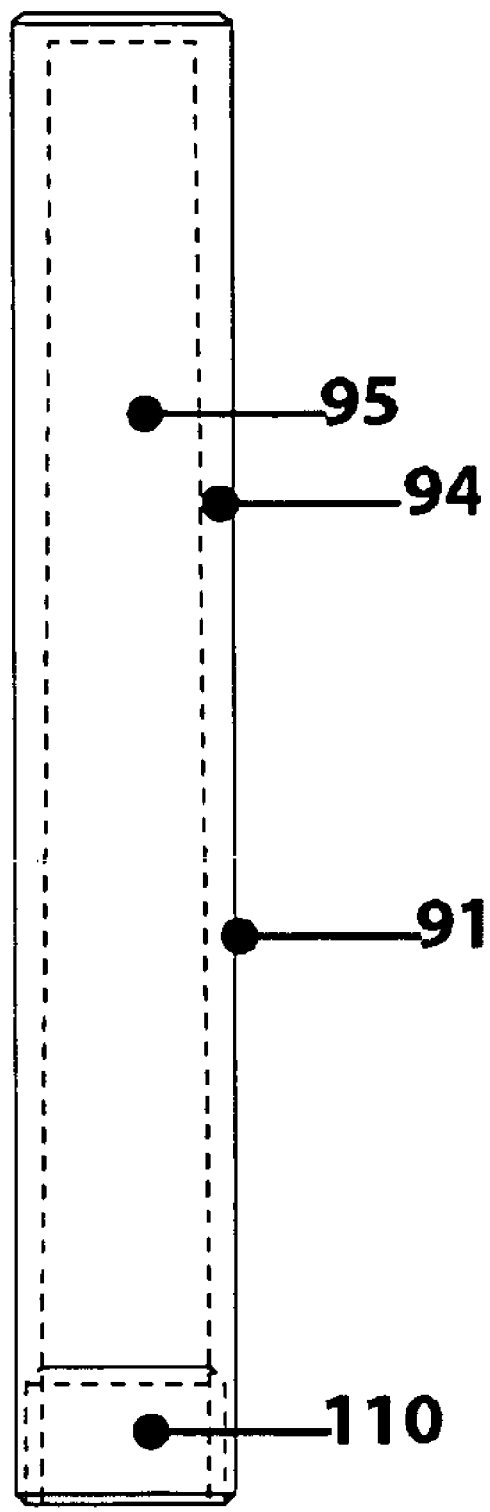

FIG. 11 refers to a longitudinal cross section of the cap or container which may hold a substance as referred to in FIG. 6.

Figure 12:
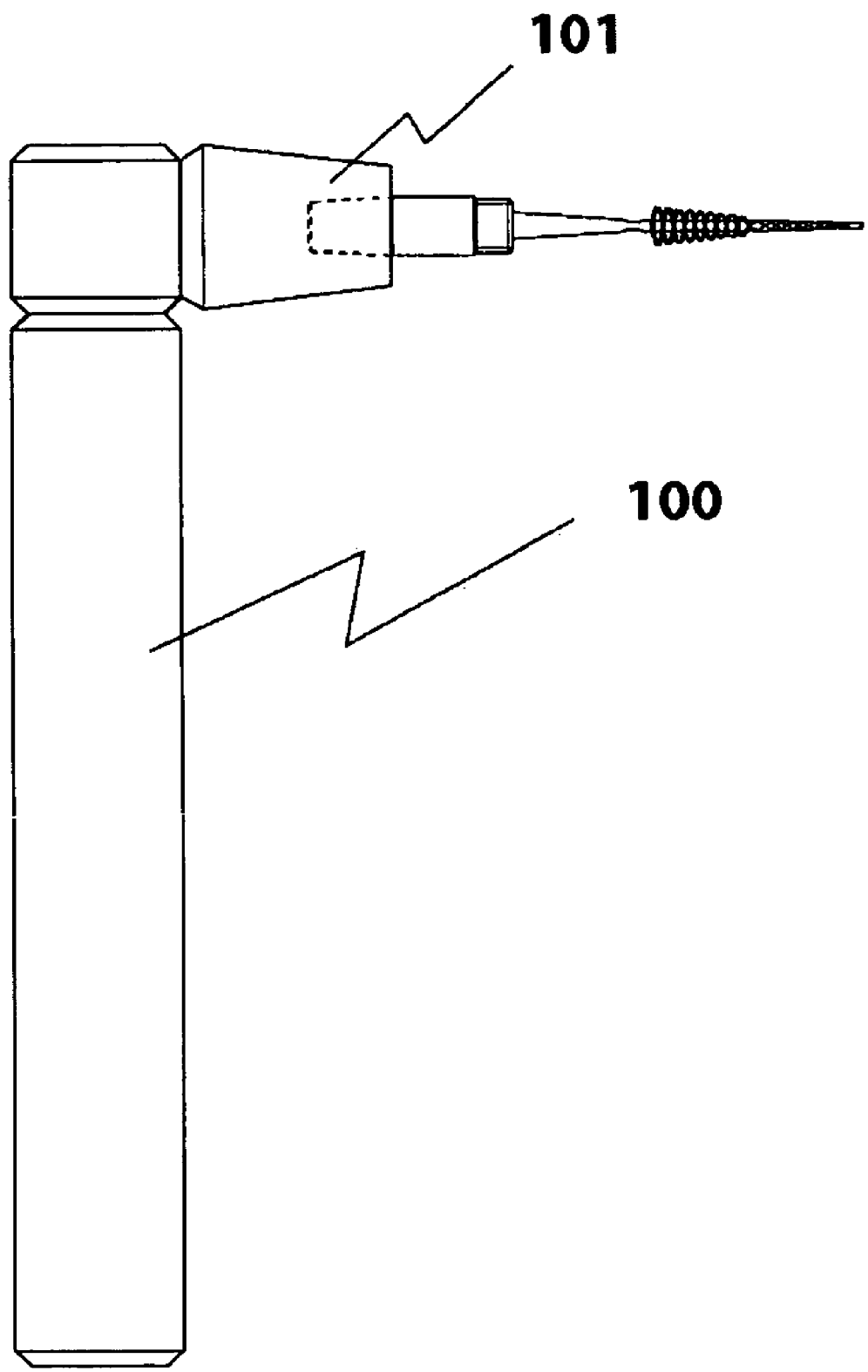

FIG. 12 refers to a motorized handle to which the tooth cleaner/drug delivery device releasably attaches, and said handle can rotate the tooth cleaner/drug delivery device clockwise to clean the area between the teeth or counterclockwise to deliver substances to the area between teeth.

In the drawings, preferred embodiments of the invention are illustrated by way of example. It is to be expressly understood that the description and drawings are only or purposes of illustration and as an aid to understanding, and are not intended to be a definition of the limits of the invention.

DETAILED DESCRIPTION OF SEVERAL PREFERRED EMBODIMENTS OF THE INVENTION

Figure 1:
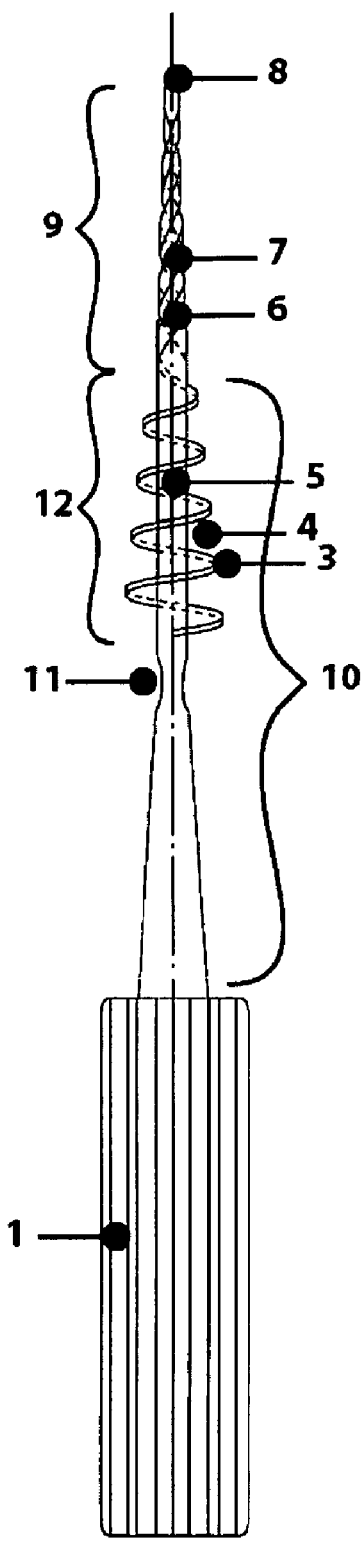
FIG. 1 represents a side view of the inter dental tooth cleaner (device) consisting of a handle, stem, and tip and extending from the stem are a (first) single helix of flanges which are arranged in a spiral pattern and are continuous with the spiral pattern of the grooves of the tip. The spiral pattern is arranged in a clockwise manner so that when the device is placed into the inter proximal area and when the handle is then rotated in a clockwise manner, the flanges and the grooves of the device withdraw plaque and food and debris from the inter dental area utilizing a screw or router type action.

FIG. 1. The handle 1 of the device is ribbed and allows for a good grip and easy rotation of same. Extending from it is a stem 10 which tapers toward the tip 9. The stem 10 has a narrowing 11 approximately midway between the handle 1 and the tip 9, and allows for bending of the device to access hard to reach areas of the mouth, (especially in the posterior regions) and coincident rotation of the flange 12 and the groove 6 and the end of the tip 8 as the handle 1 is rotated. The area 4 between turns 3 of the flange 12, as well as the grooves 6, in the tip 9 of the device will transport food and bacteria and debris out from the inter dental area as the device is rotated clockwise and will hold and transport substances to the inter dental space as the device is rotated counterclockwise, and will leave said substances in the inter dental space without being removed as the device is rotated counterclockwise, as it is being withdrawn from the inter dental area. The flange 12 may be tapered or cylindrical. The stem 10 may be deformably rigid for cleaning the area between teeth by turning said device clockwise and may be dipped into substances, for instance but not limited to a medicament or antiseptic or fluoride or varnish, and be held within the spaces 4 between turns 3 of the flange 12, the groove 6, and transported to the area between the teeth by turning said device counterclockwise, and deposited there without being withdrawn as the device is removed. The handle 1, and stem 10, may be continuous and hollow to hold substances within the interior of the device and said substance can be transported to the area between the teeth and expressed out the holes 5 which are located between turns 3 of the flange 12. The spiral configuration of the flange 12 is continuous with the groove 6 of the tip 9 to allow a continuous uninterrupted flow of debris and plaque when the device is rotated clockwise to perform cleaning actions, or to transport or deliver substances to the area between the teeth as the device is rotated counterclockwise.

Figure 2:
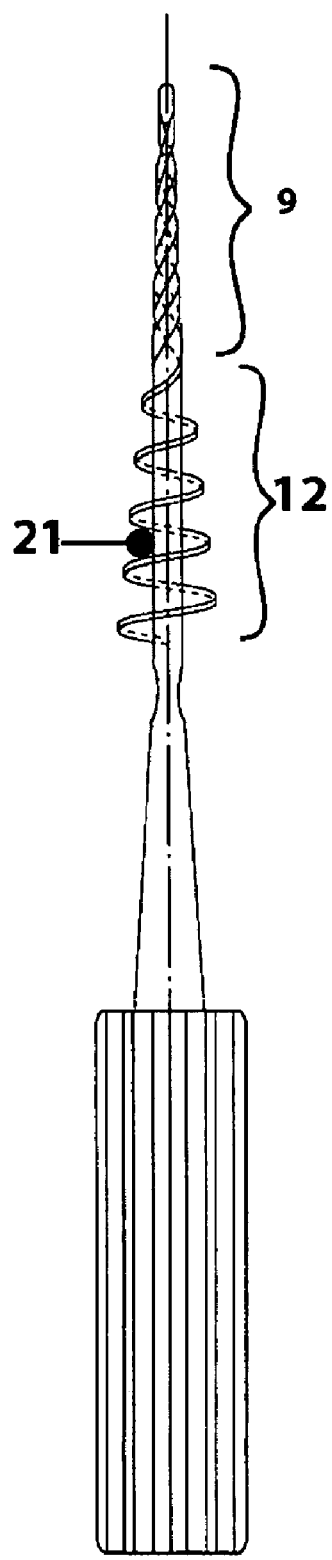
FIG. 2. Is similar to FIG. 1 indicating a (second) single helix of flanges and grooves which is very slightly offset from the first single helix.

FIG. 2 refers to the second embodiment of a helix which is slightly offset so that the space 21 between turns of the flange 12 is located slightly closer to the tip 9 of the device. The flange 12 is spirally arranged in a preferred embodiment of this invention in the shape of a cone but can be arranged spirally in other shapes for example but not limited to a cylinder.

Figure 3:
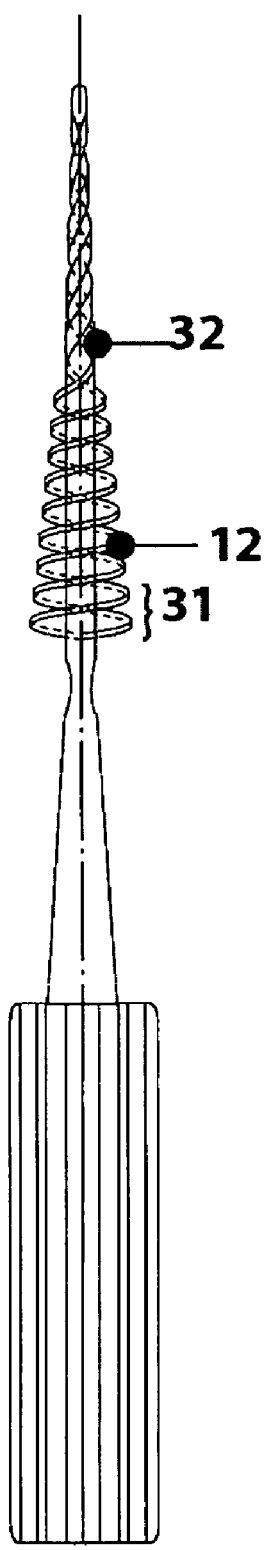
FIG. 3. Represents a combination of FIGS. 1 & 2 indicating a combination of both single helices of flanges and grooves (double helix) which increases the efficiency of action.

FIG. 3 refers to the device which has both first and second spiral combined in a continuous spiral manner so that there are a greater number of spaces between turns of the flanges 31, and grooves 32, and a greater surface area to clean and hold and transport substances.

Figure 4:
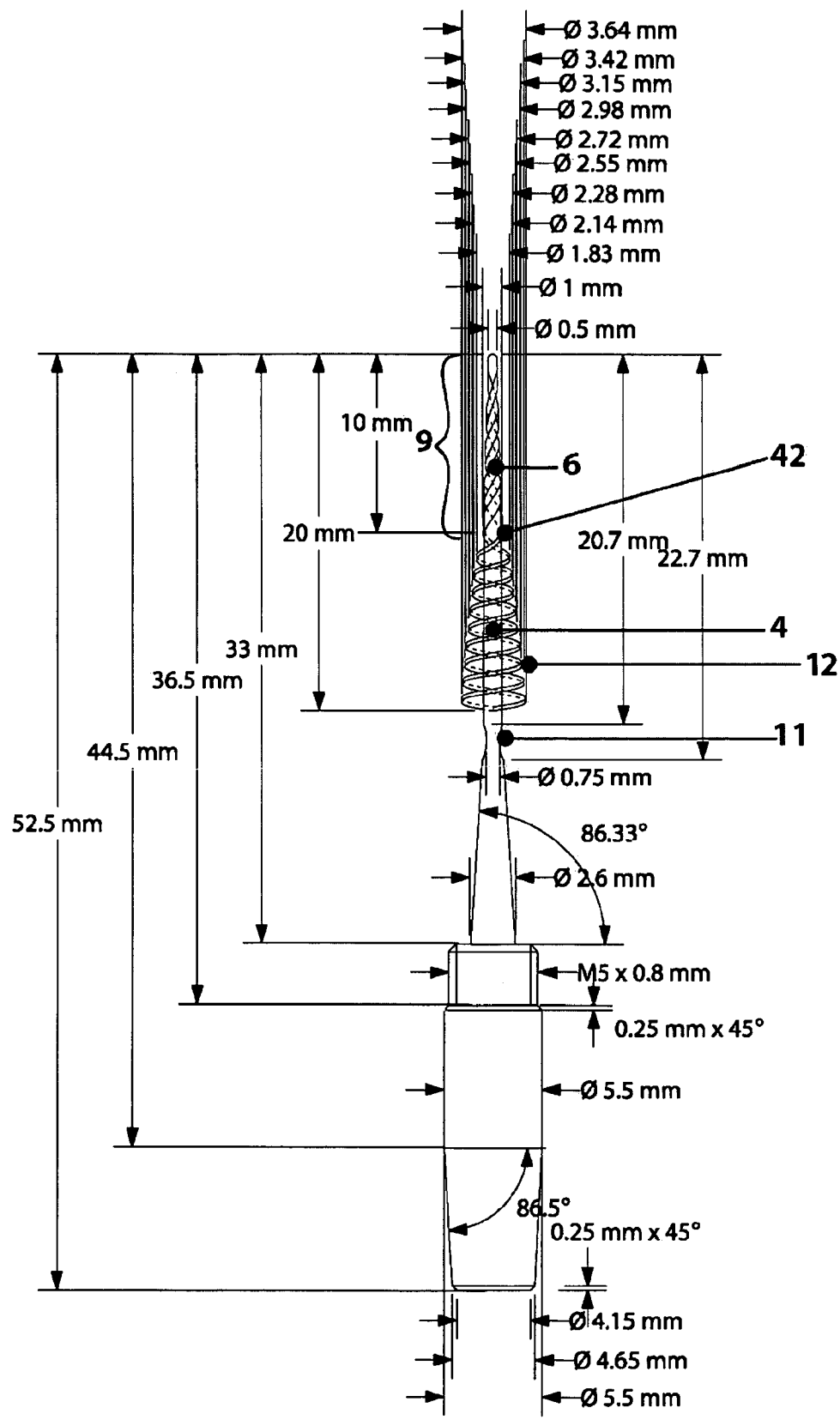
FIG. 4. Represents a longitudinal view of a preferred embodiment of the inter proximal tooth cleaner. Note that the measurements indicated are not intended to be absolute but rather indicate approximations of a preferred embodiment of this invention.

FIG. 4. Refers to the measurements of a preferred embodiment of the shape of the cleaning device as well indicating the spiral continuation 42 of the flange 12 as it meets the groove 6 of the tip 9.

Figure 5:
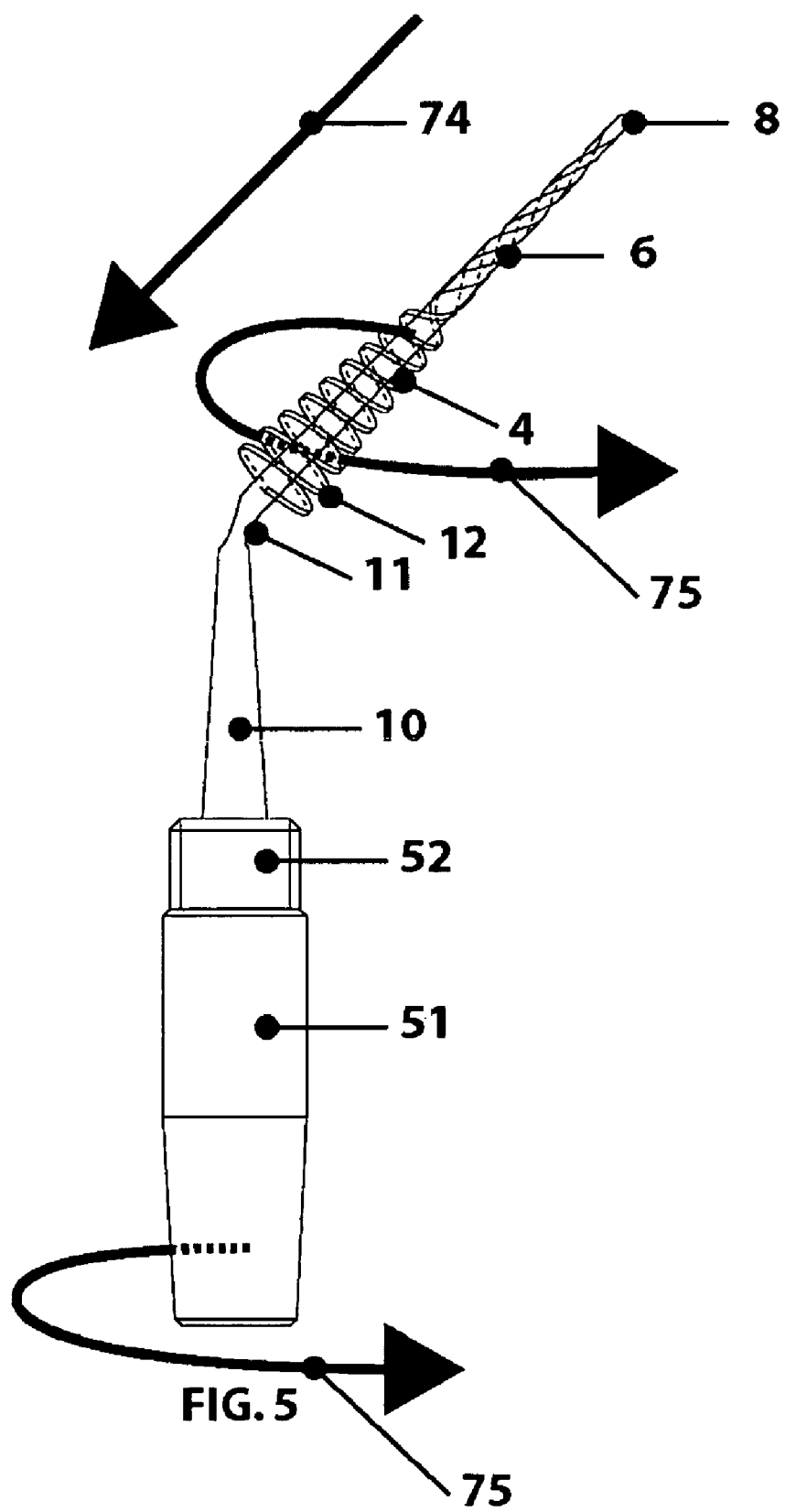
FIG. 5 represents a longitudinal view of a tooth cleaner (device) which has a slight bend in the stem so as to gain access to posterior areas of the mouth and indicates that as the handle is rotated clockwise the flanges and grooves also rotate creating a screw like cleaning action between the teeth. The spiral pattern of the flanges and grooves draw out the bacteria (plaque) and food and debris in the direction from the tip to the handle.

FIG. 5 refers to the action of rotation of the tooth cleaning device with a bend 11 in the distal part of the stem 10 which allows rotation of the flanges 12 and grooves 6 as the handle 51 is rotated. This bend 11 may be spiral or helical or be comprised of a different material such as rubber or metal or other type of plastic or silicone. The indentation 11 facilitates the rotation from the handle 51 to the flanges 12 and the grooves 6 around the neck of the device which is bent to gain access to the hard to reach posterior segments of the mouth. The device is inserted between the teeth and rotated in a clockwise direction 75 thereby engaging the grooves 6 and/or the flanges 12 between the teeth thereby capturing and transporting food, bacterial plaque and debris in a screw like manner, out from the area between the teeth in the direction 74 from the device tip 8 to the handle 51. The neck of the handle 52 may engage the interior aspect (not shown) of the device cover.

FIG. 6. Refers to a tooth cleaner and drug delivery device which acts as a tooth cleaner when the handle 61 is rotated clockwise (not shown) and as a drug delivery device when the handle is rotated counterclockwise 73. As the handle 61 which is hollow 62 contains a substance for instance but not limited to a medicament or antiseptic or fluoride or varnish, is squeezed, positive pressure is exerted on said substance which travels 71 down the hollow stem 64 and out the holes 5 between in area 4 between turns 3 of the flanges. As the handle is rotated counterclockwise 73, said substance is pushed or transported along the channels 4 formed by the spiral arrangement of said flanges towards the tip 9 of the device and then is deposited in the area between the teeth and as the handle 61 continues to be turned counterclockwise, said material is left between the teeth and is not withdrawn as the device is removed. For small inter proximal areas such as found between anterior or crowded teeth in which only the narrow tip 9 of the device will fit, the substance travels out the holes 5 between the flanges and is carried or transported to the tip 9 of the device where the grooves 6 continue to carry or transport said material in the direction 72 towards the end of the tip 8 to the inter proximal area and deposit same without being removed as the device is withdrawn. The substance travels down the continuation 42 of the spiral flanges into the grooves 6 of the tip 9 which is solid and very thin and can therefore enter between the narrow inter dental space of anterior and crowded teeth and deposit substances in these hard to reach areas. The handle 61 can be made of a semi rigid deformable material which can contain a substance which when squeezed exerts a positive pressure thereby causing said substance to travel down the hollow stem 64 out the holes 5 in the direction 71 towards the tip 9 of the device. The part 63 of the handle 61 which is proximal to the flanges may be very slightly tapered so that the opening (not shown) of the cover 82 (see FIG. 8) of the device, can fit over said taper to secure the cover to the device by a friction lock or screw type attachment.

FIG. 7. Refers to the longitudinal cross section a preferred embodiment of the tooth cleaner/drug delivery dispenser. It should be noted that all measurements are approximations of this preferred embodiment.

FIG. 8 refers to the cover 82 which may act as to protect and keep clean the device or may also contain a substance as in FIG. 6 which will coat and be carried in the flanges and grooves of the device which can then be transported to the inter proximal area. The cover 82 is releasably secured to the handle 80 of the device by way of example, friction locking or screw retained, snap on or other manner.

FIG. 9 refers to a longitudinal cross section of the cover of the device demonstrating how the cover 82 may be secured or attached to the handle 80 of the device whereby the inner proximal surface 91 of the cover 82 locks with the outer distal surface 90 of the handle 80 and how the substance as, can be contained within said cover 82.

FIG. 10 refers to the device which has been separated from its cover shown in FIG. 11. The open end 110 of the cover attaches to the proximal base 90 of the handle in a tight manner creating a seal to prevent spillage of substances within the cover 95 and forming a protective barrier from contaminating said device. The stem 92 and flanges 12 and the tip of the device as shown in FIG. 10 may be covered and protected by the cover as shown in FIG. 11 and said cover has an outer shell 94 and an inner cavity 95 which can function to keep clean and protect said inter dental cleaner or function to contain a substance for instance but not limited to a medicament or antiseptic or fluoride or varnish, or any combination thereof; when the device is placed inside the cover 94, the substance coats and is held or stored within the spiral arrangement of the flanges and grooves of the tip (refer to FIG. 1), and when said device is withdrawn from the inner cavity 95 of the handle, the substance is carried to the space between the teeth and is deposited there as the tip is inserted between the teeth (not shown).

FIG. 12 refers to a handle 100 with a motorized head 101 which rotates said device in a clockwise and counterclockwise direction which renders the device more efficient to remove the plaque and the food and the debris from the inter dental space. The device can be attached to the head of the motorized handle by a friction lock or screw or male/female type or other type of attachment.

The above description of preferred embodiments should not be interpreted in a limiting manner since other variations, modifications, and refinements are also possible with the spirit and scope of the present invention. The scope of the invention is defined in the appended claims and their equivalents.

I claim:

1. An inter-dental device comprising:
   a handle;
   a stem disposed on the handle, at least a portion of the stem being suitable for insertion into an area between two teeth,
      the stem having a tapered tip, the tip having a first helical groove therein extending from a first distal point towards the handle at least one complete turn to a first juncture point,
      the stem having a first helical flange projecting outward therefrom, the first helical flange extending away from the handle from a first proximal point towards the tip and terminating at the first juncture point where the first helical groove begins such that the first helical groove and the first helical flange are not intertwined and form a first continuous single helix, the first helical flange tapering towards the tip;
   whereby the area between the teeth may be cleaned by insertion of at least a portion of the device between the teeth.

2. The inter-dental device of claim 1, wherein the first continuous single helix continuously tapers towards the tip.

3. The inter-dental device of 1, wherein
   the tip further has a second helical groove therein offset from the first helical groove extending from a second distal point towards the handle at least one complete turn to a second juncture point,
   the stem further has a second helical flange projecting outward therefrom offset from the first helical flange, the second helical flange extending away from the handle from a second proximal point towards the tip and terminating at the second juncture point where the second helical groove begins such that the second helical groove and the second helical flange are not intertwined and form a second continuous single helix offset from the first continuous single helix, whereby the first continuous single helix and the second continuous single helix together form a double helix, the second helical flange tapering towards the tip.

4. The inter-dental device of claim 3, wherein the second continuous single helix continuously tapers towards the tip.

5. The inter-dental device of claim 3, wherein the stem further has a hole allowing for the dispensing of material therethrough.

6. The inter-dental device of claim 3, wherein the stem further has a plurality of holes allowing for the dispensing of material therethrough, each of the holes being located on the stem between turns of the first helical flange.

7. The inter-dental device of claim 6, wherein the stem further has central hollow chamber fluidly connected to the holes.

8. The inter-dental device of claim 3, further comprising a cover removably connectable to the handle for covering the stem.

9. The inter-dental device of claim 8, wherein the cover has a reservoir therein constructed and arranged such that when the cover is connected to the handle, at least a portion of the stem is in communication with material in the reservoir.

10. The inter-dental device of claim 3, wherein the stem has a dimple therein allowing the stem to be bent relative to the handle.

11. The inter-dental device of claim 3, wherein the handle has a motor for driving rotation of the stem.

12. The inter-dental device of claim 11, wherein the stem has a dimple therein allowing the stem to be bent relative to the handle and allowing the stem to be maintained in its orientation relative to the handle while the motor is driving rotation of the stem.

13. The inter-dental device of claim 1, wherein the stem further has a hole allowing for the dispensing of material therethrough.

14. The inter-dental device of claim 1, wherein the stem further has a plurality of holes allowing for the dispensing of material therethrough, each of the holes being located on the stem between turns of the first helical flange.

15. The inter-dental device of claim 14, wherein the stem further has central hollow chamber fluidly connected to the holes.

16. The inter-dental device of claim 1, further comprising a cover removably connectable to the handle for covering the stem.

17. The inter-dental device of claim 16, wherein the cover has a reservoir therein constructed and arranged such that when the cover is connected to the handle, at least a portion of the stem is in communication with material in the reservoir.

18. The inter-dental device of claim 1, wherein the stem has a dimple therein allowing the stem to be bent relative to the handle.

19. The inter-dental device of claim 1, wherein the handle has a motor for driving rotation of the stem.

20. The inter-dental device of claim 19, wherein the stem has a dimple therein allowing the stem to be bent relative to the handle and allowing the stem to be maintained in its orientation relative to the handle while the motor is driving rotation of the stem.

21. The inter-dental device of claim 20, wherein the motor is reversible so as to be capable of driving rotation of the stem in both clockwise and counterclockwise directions.

* * * * *